US00PP37685P2

(12) United States Plant Patent
Hansen

(10) Patent No.: US PP37,685 P2
(45) Date of Patent: Sep. 8, 2026

(54) ***PERSICARIA* PLANT NAMED 'Glowing Reviews'**

(50) Latin Name: ***Persicaria amplexicaulis* (D. Don) Ronse Deer.**
Varietal Denomination: Glowing Reviews

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 40 days.

(21) Appl. No.: 18/831,965

(22) Filed: Dec. 11, 2025

(51) Int. Cl.
*A01H 6/00* (2018.01)
*A01H 5/02* (2018.01)

(52) U.S. Cl.
USPC ..... Plt./467

(58) Field of Classification Search
USPC ..... Plt./467
CPC ..... A01H 6/00; A01H 5/02
See application file for complete search history.

*Primary Examiner* — Keith O. Robinson

(57) ABSTRACT

A new and distinct *Persicaria* plant named 'Glowing Reviews' characterized by vibrant cerise-red flowers that emerge from dark red buds, held on long, dense, inflorescence spikes above golden-chartreuse lanceolate foliage that goes dormant in the winter. Flowers begin in late summer and spikes remain in flower until kill frost.

1 Drawing Sheet

Botanical classification: *Persicaria amplexicaulis* (D. Don) Ronse Decr.

Variety denomination: 'Glowing Reviews'.

STATEMENT REGARDING PRIOR DISCLOSURES UNDER 37 CFR 1.77(b)(6)

The first private offers for sale of *Persicaria* 'Glowing Reviews' were to Overdevest Nurseries, LP, Prides Corner Farms, and Saunder Brothers, Inc. by Walters Gardens, Inc. on Dec. 11, 2024. Walters Gardens, Inc. obtained the new plant and information about the new plant directly from the inventor. No plants of *Persicaria* 'Glowing Reviews' have been sold, in this country or anywhere in the world, nor has any disclosure of the new plant been made more than one year prior the filing date of this application and such sale or disclosure within one year was either derived directly or indirectly from the inventor and would therefore be a 35 USC 102(b) exception.

BACKGROUND AND ORIGIN OF THE PLANT

The present invention relates to a new and distinct mountain fleece plant, *Persicaria* 'Glowing Reviews', hereinafter also referred to as the "new plant" or just the cultivar name 'Glowing Reviews'. *Persicaria* 'Glowing Reviews' is a cross between 'Amethyst Summer' (not patented) as the female or seed parent and 'Golden Arrow' (not patented) as the male or pollen parent in a greenhouse at a wholesale perennial nursery in Zeeland, Michigan, USA. The cross was made on Oct. 1, 2021, and seed was collected on Dec. 6, 2021. The new plant was selected as a single seedling from this cross and after confidential evaluations in a trial bed beginning in 2022 in Zeeland, MI and was assigned the breeder code 21-3-1 through the remaining trial period.

The new plant has been asexually propagated by division and shoot tip cuttings at the same wholesale nursery in Zeeland, MI since 2023 with all the resultant asexually propagated plants shown to retain all the same unique traits as the original plant. 'Glowing Reviews' has proven to be stable and reproduces true to type in successive generations of asexual reproduction.

The most similar known mountain fleece plant cultivars are: 'Blackfield' U.S. Plant Pat. No. 17,635, 'Fat Domino' U.S. Plant Pat. No. 17,467, and 'Flamingo Feathers' U.S. Plant Pat. No. 33,833.

'Blackfield' has darker green foliage and darker reddish flowers. 'Fat Domino' has a larger habit, darker green foliage, and more reddish-purple flowers. 'Flamingo Feathers' has a larger habit, larger and more greenish foliage, and the flowers are a lighter pinkish-red color.

The female parent, 'Amethyst Summer', is taller and the flowers are a deep pink. The male parent, 'Golden Arrow' has more golden and less chartreuse foliage, fewer inflorescences. per plant, and begins flowering later in the season.

*Persicaria* 'Glowing Reviews' differs from all other mountain fleece plants known to the applicant, by the combination of the following traits:

1. Vibrant cerise-red flowers emerge from dark red buds;
2. Long season of bloom beginning in late summer and continuing until killing frost;
3. Golden chartreuse lanceolate foliage holds up under full sun conditions;
4. Vigorous growth with dense flower spikes.

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
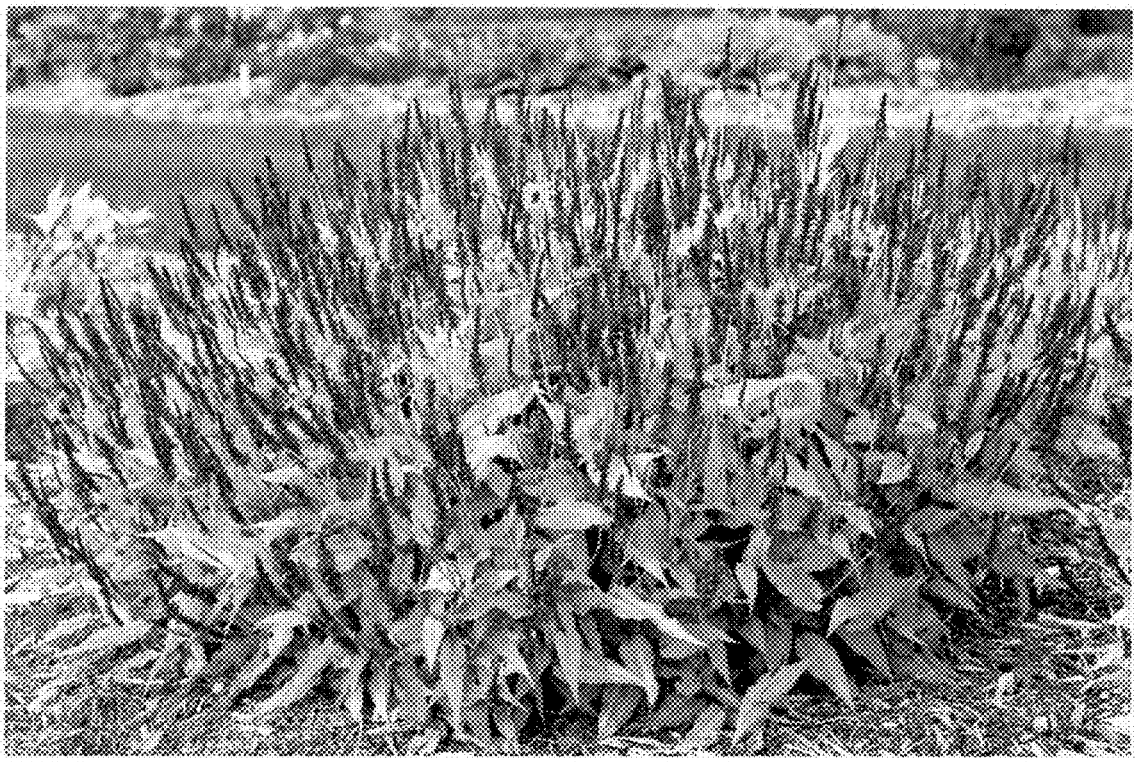
FIG. 1 shows a two-year-old plant in peak flower in early autumn in a full-sun trial garden in Zeeland, Michigan.
Figure 2:
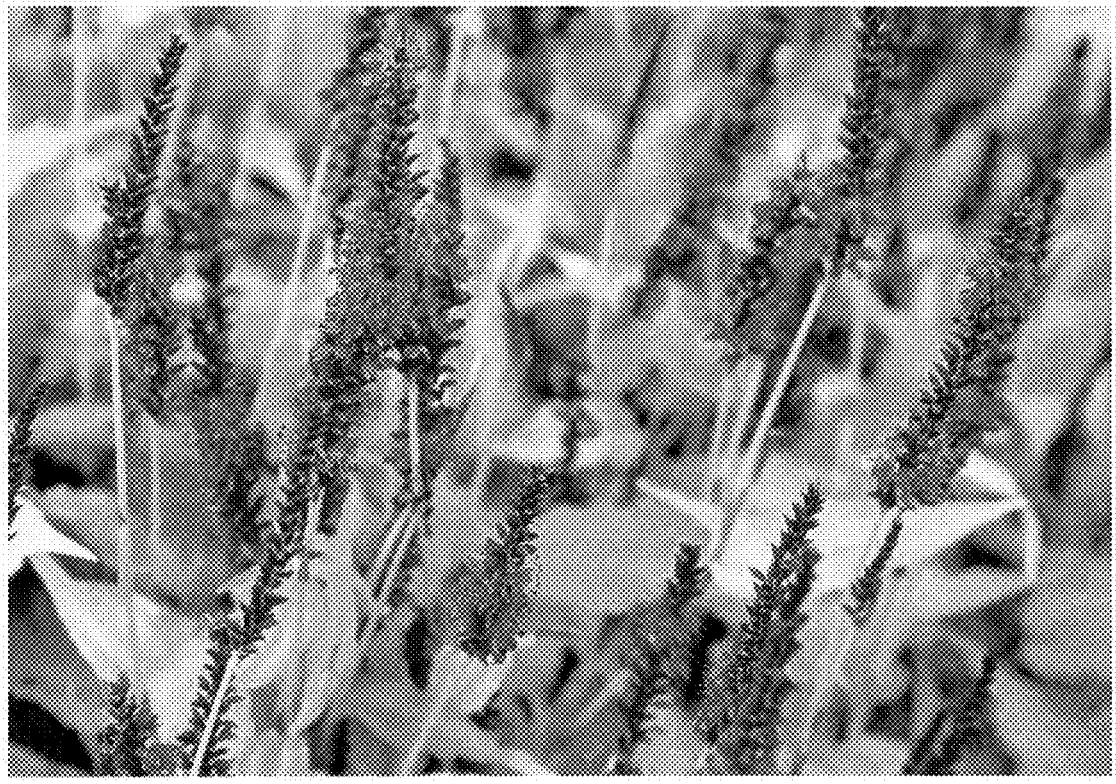
FIG. 2 shows a close-up of the flower and buds.

The following detailed description of *Persicaria* 'Glowing Reviews' is of a two-year-old plant growing in a partially-shaded greenhouse and a four-year-old plant growing in a full sun trial garden in Zeeland, MI, both with limited supplemental fertilizer and irrigation as needed and without any pinching or plant growth regulators. The new plant has not been observed under all possible environments, and the phenotype may vary slightly with different environmental conditions, such as temperature, light, fertility, moisture, and maturity levels, but without any change in the genotype. The color descriptions are in accordance with the 2015 edition of The R.H.S. Colour Chart of The Royal Horticultural Society, except where common dictionary color terms are used.

Parentage: Female or seed parent is 'Amethyst Summer', male or pollen parent is 'Golden Arrow';

Plant habit: Multi-stemmed herbaceous perennial; upright to broadly spreading;

Plant size: Flowering to about 83 cm tall, 109 cm wide at ground level, with base about 30 cm across;

Propagation: Cuttings; time to produce a rooted young plant about 3 weeks at temperatures of about 20° C. and time to produce a finished flowering plant in a 3.8-liter container about 11 weeks at temperatures fluctuating between 12° and 28° C.;

Roots: Fibrous becoming slightly fleshy; freely branching; dense;

Root color: Young active roots nearest RHS NN155C, older more fleshy roots variable, between RHS 165D and RHS NN155D, and between RHS 173D and RHS NN155D;

Stem: About 200 per four-year-old plant; terete; fistulose; glabrous; slightly lustrous; inner stems erect, outer stems outwardly becoming erect distally; to about 75 cm long below terminal inflorescence and 4 mm diameter at base;

Stem color: Nearest RHS 2D proximally and between RHS N144D and RHS 145B distally;

Nodes: About 7 per stem below terminal inflorescence; swollen to about 5 mm diameter; internode length about 9.5 cm;

Node color: Nearest RHS 2D proximally and between RHS N144D and RHS 145B distally;

Branches: Freely branching with about 3 inflorescence spikes per stem; glabrous; slightly lustrous; to about 15 cm long and 1.5 mm diameter; aspect about 70° above horizontal; color nearest RHS 19C;

Foliage description: Alternate; lanceolate; simple; apex narrowly acute; base cordate with lobes not imbricate; margin entire, finely undulate; adaxial matte and micro-puberulent; abaxial matte and puberulent;

Leaf size: To about 19 cm long and to about 9 cm wide, decreasing distally;

Leaf fragrance: None detected;

Venation: Pinnate; adaxial impressed, abaxial costate; adaxial midrib puberulent, adaxial primary and secondary veins glabrous, abaxial midrib, primary; and secondary puberulent;

Leaf color: Expanding adaxial nearest RHS 144A, abaxial between RHS 147C and RHS 148C; mature adaxial variable some regions nearest RHS 144A and other regions nearest RHS 154C, and between RHS 154D and RHS N144E, mature abaxial between RHS 147C and RHS 148C;

Petioles: Slightly concavo-convex; sparsely micro-puberulent and slightly lustrous adaxial and micro-puberulent and matte abaxial; to about 11.5 cm long and 10 mm across at base;

Petiole color: Basal adaxial and abaxial proximal one-quarter between RHS 160C and RHS 159B, distal adaxial portion between RHS 147C and RHS 146D, distal abaxial portion nearest RHS 145C in the longitudinal center and nearest RHS 143A along margins;

Stipules: One; lanceolate; hyaline; at the base of each leaf; glabrous; apex narrowly acute, base clasping; margin entire; to about 5.2 cm long and about 1.1 cm wide;

Stipule color: Nearest RHS 165A;

Inflorescence: In terminal racemes; to about 10 cm long and 2 cm diameter; to about 300 flowers developing per inflorescence and about 600 flowers per stem;

Flower buds: Flattened ovoid; rounded apex; rounded base; to about 5 mm long, 2.5 mm across, and 2 mm thick near base; glabrous; matte;

Flower bud color: Between RHS 58A and RHS 53A;

Flower: Single; rotate; perfect; incomplete; freely flowering; aspect mostly outwardly; to about 9 mm across and 7 mm deep to exserted style; corolla to 9 mm across and about 2 mm deep; not persistent;

Fragrance: None detected;

Flowering season: Plants flower naturally from late summer to fall frost for about eight weeks; individual flowers last about one week on the plant;

Tepals: Five; arranged in a single whorl; ovate; acute apex, base truncate and connate in the proximal 1.5 mm; margin entire, not undulate; glabrous adaxial and abaxial; slightly concave; to about 4 mm long and 2 mm wide just above fusion;

Tepal color: When first opening adaxial between RHS 53D and RHS 54A and abaxial between RHS 53A and RHS 58A; when fully opened adaxial nearest RHS 63B, abaxial between RHS 53A and RHS 58A venation, close to between 58C to 58D;

Peduncle: Terete; fistulose; glabrous; slightly lustrous; strong; to about 12 cm long and 3 mm diameter at base and 2 mm diameter just below flowers; aspect erect;

Peduncle color: Nearest RHS 151A;

Pedicel: Terete; fistulose; glabrous; about 6 mm long and 0.5 mm diameter; moderately strong; aspect: About 45° above horizontal;

Pedicel color: Proximally nearest RHS 58D, distally between RHS 58A and RHS 63B;

Floral bracts: Single large bract subtending a cluster of three to five flowers and single small bract subtending individual flowers; large bract lanceolate, hyaline, with narrowly acute apex and truncate base, to about 8 mm long and 4 mm wide at base, decreasing in size distally on spike, color transparent to nearest RHS 166D; small bract lanceolate, hyaline, with narrowly. acute apex and truncate base, to about 4 mm long and 1.5 mm wide at base, color transparent with slight RHS 166D blush;

Androecium: Eight;

*Filament*.—Cylindrical; glabrous; straight; to about 3 mm long and 0.3 mm diameter; color distally between RHS 58A and RHS 63B, proximally nearest RHS 58D.

*Anther*.—Ellipsoidal; dorsifixed; longitudinal; about 1 mm long and 0.5 mm across; color: RHS 92A.

*Pollen*.—Quantity moderate; color: nearest RHS N187C.

Gynoecium: Superior;

*Style*.—Three; cylindrical; thin; straight; about 3 mm long and 0.1 mm diameter; color nearest RHS 63A.

*Stigma*.—Acute; about 0.1 mm across; color nearest RHS 63A.

*Ovary color*.—Oblong; to about 2 mm long and 1 mm across; acute apex; truncate base; color between RHS 147C and RHS 144B.

Fruit: Not observed under present growing conditions;

Seed: Not observed under present growing conditions;

Pathogen and pest resistance: Plants of the new *Persicaria* have not been observed to be resistant to pathogens and pests common to *Persicaria* plants.

Garden performance: 'Glowing Reviews' plants exhibited good garden performance, hardiness in USDA Zones 5 to 10, and best suited where protected from harsh sun as a specimen plant or en masse;

Disease and pest resistance, tolerance and susceptibility: 'Glowing Reviews' tends to be susceptible to *Tetranychus* sp. spider mites in greenhouse conditions, but has not shown resistance or susceptibility to other diseases and pests beyond that common for mountain fleece plants.

I claim:

1. A new and distinct ornamental plant cultivar named *Persicaria* 'Glowing Reviews' as herein described and illustrated.

* * * * *